United States Patent [19]
Silver et al.

[11] Patent Number: 5,413,564
[45] Date of Patent: May 9, 1995

[54] PREDETERMINED DOSAGE HYPODERMIC SYRINGE SYSTEM

[76] Inventors: Jules Silver, 7 Ridgewood Rd., Niantic, Conn. 06357; Louis C. Ziegler, 5 Skyline Dr., Englewood Cliffs, N.J. 07632

[21] Appl. No.: 204,950
[22] Filed: Mar. 2, 1994
[51] Int. Cl.[6] .................................................. A61M 5/00
[52] U.S. Cl. .................................. 604/232; 604/212; 604/110
[58] Field of Search .............. 604/232, 233, 234, 235, 604/218, 187, 221, 222, 212

[56] References Cited

U.S. PATENT DOCUMENTS

| | | | |
|---|---|---|---|
| 1,738,146 | 12/1929 | Kulik | 604/232 |
| 4,236,516 | 12/1980 | Nilson | 604/235 X |
| 4,392,491 | 7/1983 | Takasugi et al. | 604/234 X |
| 5,019,046 | 5/1991 | Kohler | 604/218 |
| 5,026,346 | 6/1991 | Spanner et al. | 604/218 |

*Primary Examiner*—John D. Yasko
*Attorney, Agent, or Firm*—Burd, Bartz & Gutenkauf

[57] ABSTRACT

A hypodermic syringe system for injecting a predetermined dosage of therapeutic fluid into body tissue of a living patient. A sealed capsule contains the fluid to be injected. A double ended hypodermic needle includes a first sharpened end for piercing engagement with the body tissue and a second sharpened end opposite therefrom for piercing engagement with the capsule. The capsule is disposed between the end of a plunger which is slidably engaged within a barrel member supporting the needle and the end wall of the barrel member. Advancement of the plunger moves the capsule into piercing engagement with the second sharpened end of the needle, collapsing the capsule and discharging the therapeutic fluid through the needle and into the body tissue. A safety syringe with a retractable needle is disclosed. The system is also provided with an aspirating capability to inform the user whether or not a blood vessel has been pierced by the needle.

18 Claims, 3 Drawing Sheets

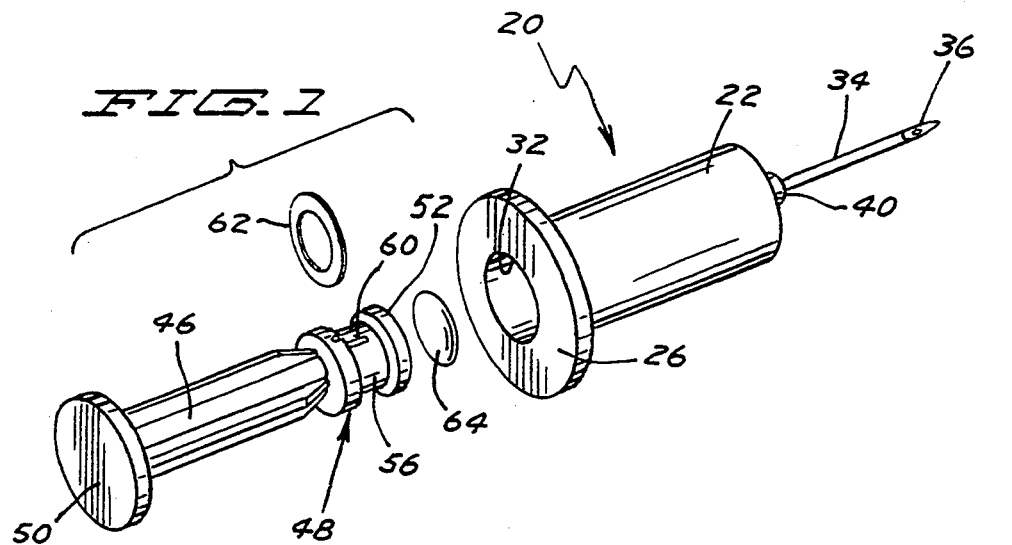
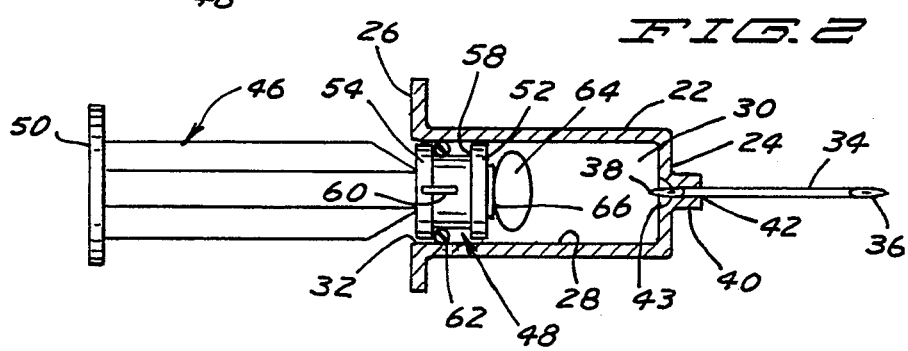
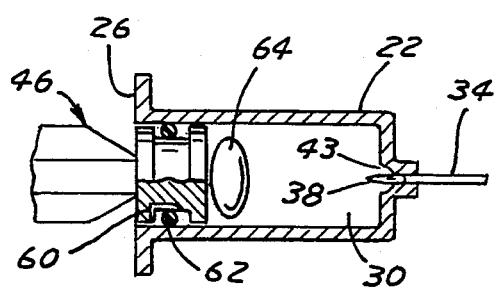 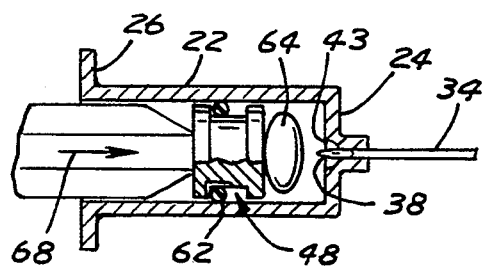
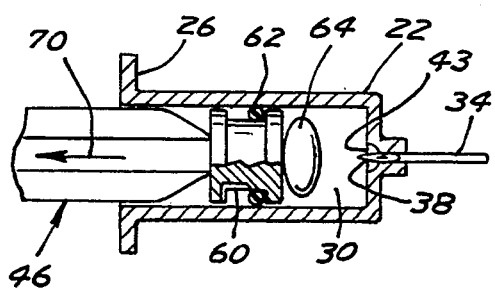 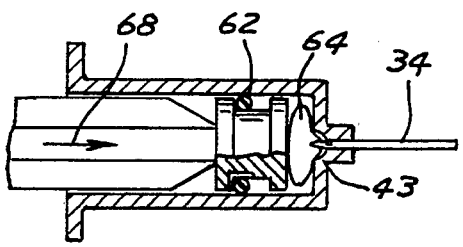

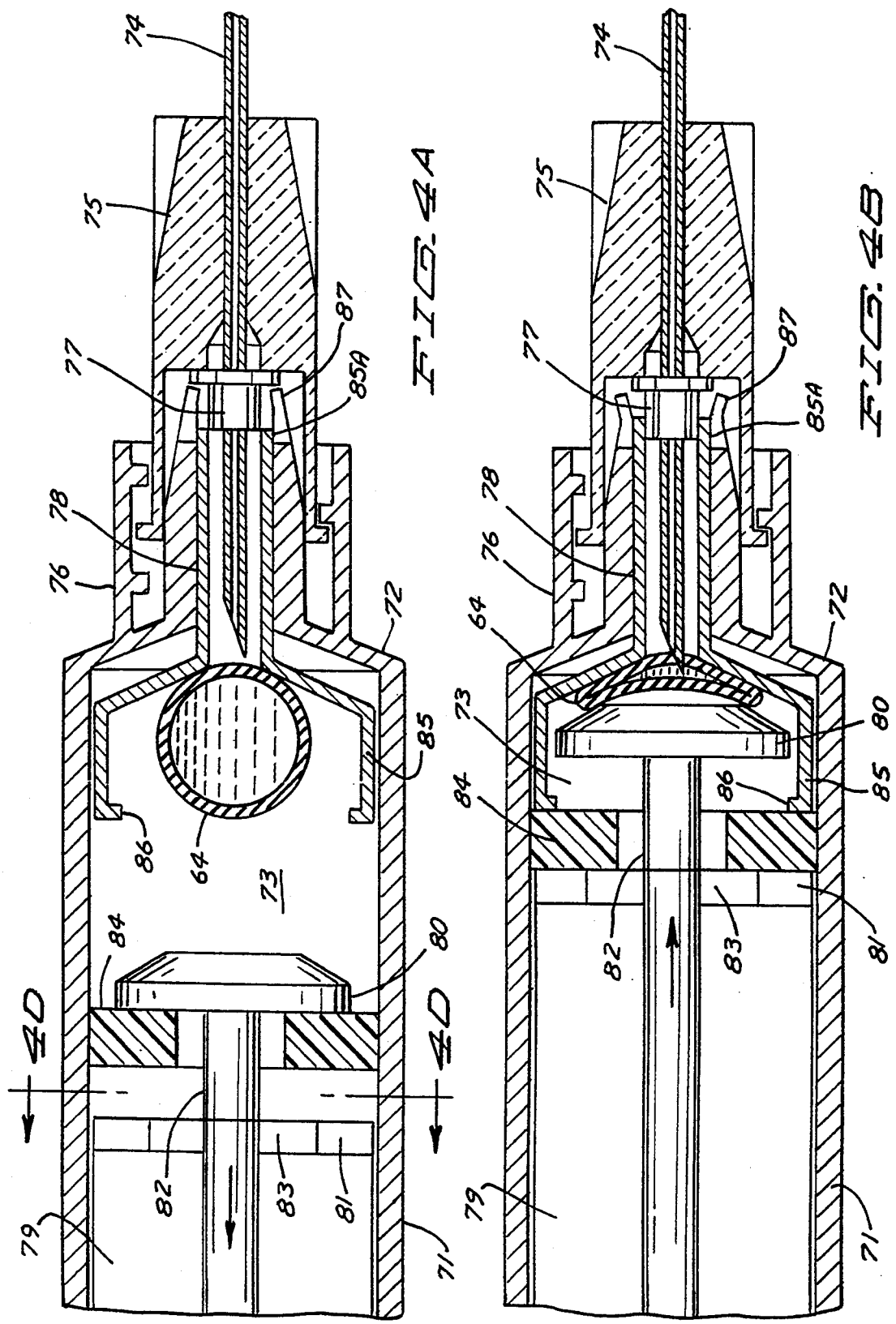

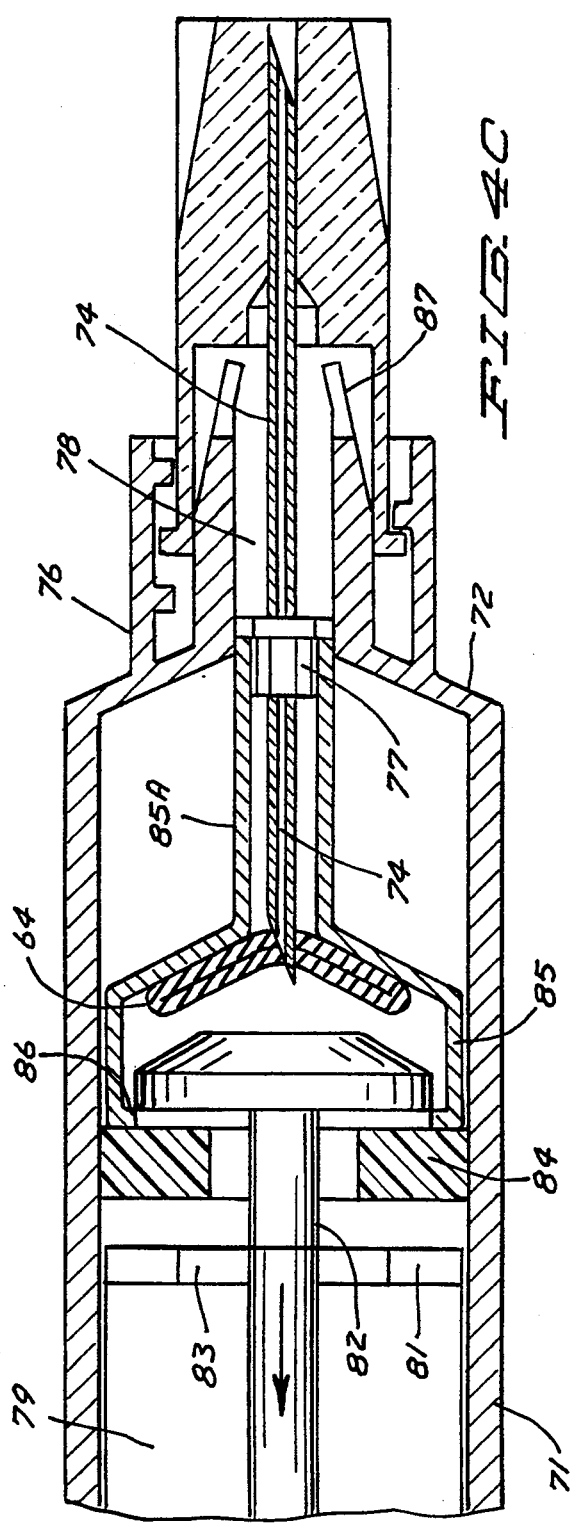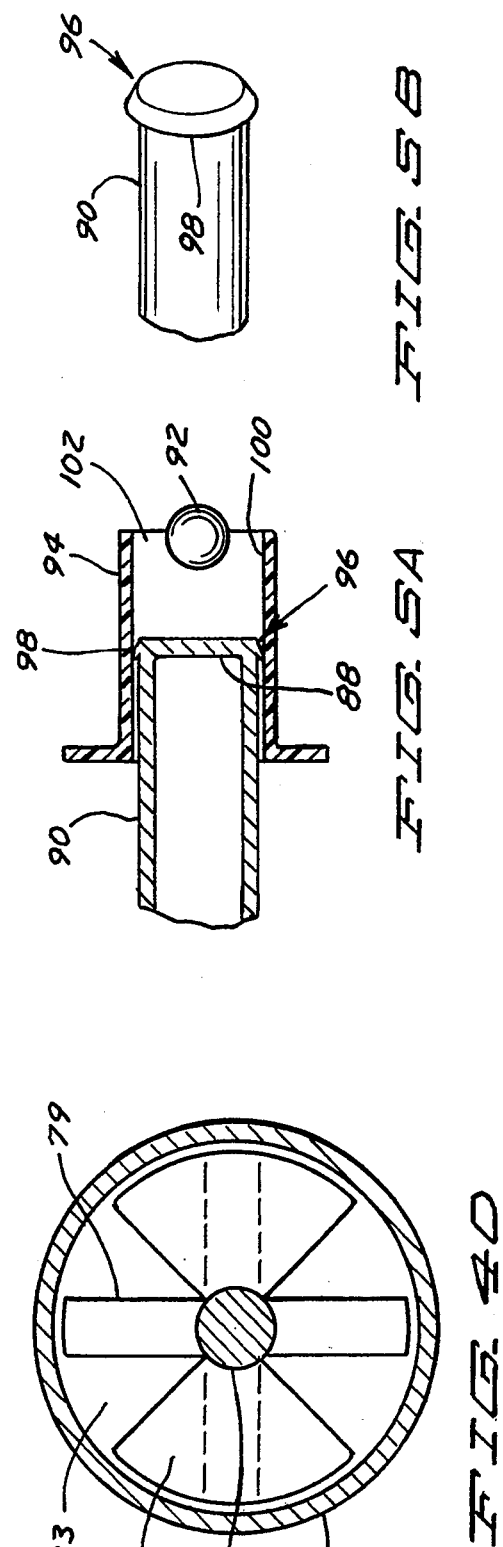

PREDETERMINED DOSAGE HYPODERMIC SYRINGE SYSTEM

BACKGROUND OF THE INVENTION

1. Field of the Invention

This invention relates generally to syringes for injecting a therapeutic liquid into a patient, human or animal, by means of a hypodermic needle. In particular, it relates to a syringe utilizing a thin-walled collapsible capsule containing a predetermined measured dosage of liquid, wherein the liquid is selectively discharged from the capsule and into and through the needle by compressing or squeezing the capsule. The system is also provided with aspirating capability to determine whether or not a blood vessel has been punctured by the needle.

2. The Prior Art

The prior art is exemplified by the following patents showing hypodermic devices utilizing collapsible or compressible bulbs or pouches or the like pre-filled with a precisely measured amount of medicament:

| U.S. Pat. No. | Patentee | Issue Date |
| --- | --- | --- |
| 798,093 | Dean | August 29, 1905 |
| 2,618,263 | Lakso, et al | November 18, 1952 |
| 3,099,264 | Hubbard | July 30, 1963 |
| 3,114,369 | Hall | December 17, 1963 |
| 4,013,073 | Cunningham | March 22, 1977 |
| 4,475,906 | Holzner | October 9, 1984 |
| 4,581,021 | Landau, et al | April 8, 1986 |

SUMMARY OF THE INVENTION

Broadly stated, the present invention is directed to a hypodermic syringe system for injecting a predetermined amount of a therapeutic fluid into the tissue of a living body. The system includes a syringe having an elongated plunger extending between a proximal end and a distal end and having a thumb plate on the proximal end and a head member on the distal end. An elongated barrel member having a longitudinal axis and extending between a distal end and a proximal end defines a chamber for slideably receiving the distal end of the plunger. The barrel member includes a front wall at the distal end, a rim at the proximal end defining an opening through which the distal end of the plunger can enter and a hub member integral with the front wall and mounting a double ended hypodermic needle including a first sharpened end for piercing engagement with the body tissue and a second sharpened end opposite from the first end, the tip of the second end extending through the front wall of the barrel member. The needle is in substantial axial alignment with the barrel member. A sealed collapsible capsule containing a predetermined dose of the therapeutic fluid to be injected is disposed in the chamber of the barrel member between the head member of the plunger and the tip of the second end of the needle.

According to one embodiment of the invention the needle may be retracted into the syringe barrel after use to prevent accidental piercing of the skin of a health care worker. The system is also provided with an aspirating capacity to create a vacuum in the chamber of the barrel member to inform the user whether or not a blood vessel has been accidentally pierced.

BRIEF DESCRIPTION OF THE DRAWINGS

The invention is illustrated by the accompanying drawings in which corresponding parts are identified by the same numerals and in which:

FIG. 1 is an exploded perspective view of one embodiment of a predetermined dosage hypodermic syringe system embodying the invention;

FIG. 2 is a side elevational view, partly in section, illustrating the system of FIG. 1;

FIGS. 3A, 3B, 3C, and 3D are fragmentary side elevational views, partly in section, similar to FIG. 2 and illustrating successive positions of the components of the system in the course of an injection procedure;

FIGS. 4A, 4B, and 4C are fragmentary cross sectional views, in elevation, illustrating three successive positions of a modified predetermined dosage hypodermic syringe system according to the invention and having means for retracting the needle into the syringe barrel after use;

FIG. 4D is a transverse section on the line D—D of FIG. 4A and in the direction of the arrows;

FIG. 5A is a fragmentary cross sectional view, in elevation, illustrating still another embodiment of the invention; and FIG. 5B is a fragmentary perspective view illustrating the sealing component of the construction illustrated in FIG. 5A.

DETAILED DESCRIPTION OF THE PREFERRED EMBODIMENTS

Referring now to the drawings, and particularly to FIGS. 1 and 2, there is shown a system 20 for injecting a therapeutic fluid into tissue of a living body in accordance with the invention. A tubular right cylindrical barrel member 22 extends between a front wall 24 at the distal end and an annular operating flange 26 at the proximal end. The barrel member 22 has an inner wall 28 which defines a chamber 30. The operating flange 26 defines an opening 32 into the chamber 30.

A hypodermic needle 34 includes a sharpened distal end 36 intended for piercing engagement with the body tissue and a sharpened proximal end 38 to be utilized in a manner to be explained below. A hub member 40 is integral with the front wall 24 and coaxial with the barrel member 22. The hub member 40 has a longitudinally extending central bore 42 therethrough for mounting the needle 34 in the conventional rigid fashion. To avoid premature piercing of the capsule containing medicament, the proximal end 38 of needle 34 is recessed in a well or other depression 43 formed in front wall 24 of the barrel member.

An elongated plunger 46, which may be of cruciform cross section, is adapted for slidable reception through the proximal opening 32 into the chamber 30 of the barrel 22. The plunger 46 extends between a head member 48 at a distal end and a thumb plate 50 at a proximal end. For its part, the head member 48 includes a pair of spaced apart, generally parallel, collar members 52, 54. The collar members 52, 54 lie in planes which are generally perpendicular to the longitudinal axis of the plunger 46. The collar member 52 may be referred to as a distal collar member and the collar member 54 may be referred to as a proximal collar member. A central core 56 of reduced diameter is defined by an annular recess 58 existing between the collar members 52, 54. It will be appreciated that the outer diameters of the collar members 52, 54 are slightly less than the inner diameter of the inner wall 28. An air flow channel 60 is formed in the central core 56 lying generally in a plane of the longitudinal axis of the plunger 46. The air flow channel 60 continues from the central core 56 radially across the distal surface of the proximal collar member 54 continuing to a discharge opening at an outer peripheral surface of the collar member 54, as best seen in FIG. 2.

An O-ring seal is received within the annular recess 58 encircling and fittingly received on the central core 56. It also is slideably, but sealingly, engaged with the inner wall 28. The seal 62 is movable on the central core 56 between positions, respectively, adjacent said distal collar member 52 and adjacent said proximal collar member 54.

The reason for the air flow channel 60 and for the O-ring seal 62 will be explained below.

A sealed thin walled collapsible capsule 64 may be mounted on the distal surface of the collar member 52 as, for example, by means of a tacky biocompatible adhesive 66. Alternatively, capsule 64 may simply be dropped into barrel 22. Capsule 64 may be gelatin or any soft pliable compressible biocompatible encapsulating plastic material which performs like gelatin and preferably will tolerate drugs with a high moisture level to a greater extent than conventional gelatin. Techniques for the manufacture of capsules have long been known and are characterized by the fact that the capsule material envelopes the liquid encapsulated therein in a manner which prevents any voids or air pockets from forming. Such capsules can be made in a variety of sizes according to the desired dosage, and shapes and colors according to the particular medicament which is contained. Capsules can also be readily marked to provide additional information, if desired.

With the plunger 46 initially withdrawn from the barrel member 22, a selected gelatin capsule 64 is inserted into the barrel by affixing to the distal surface of the collar member 52 by means of adhesive 66 or simply dropped into the barrel. Thereupon, the head member 48 of the plunger 46 is inserted into the chamber 30 of the barrel member 22 as seen in FIGS. 2 and 3A. The plunger 46 is then advanced in the direction of arrow 68 until the head member 48 attains a position well within the chamber 30 but out of piercing engagement with the proximal end 38 of the needle 34.

It is common procedure to aspirate a syringe system immediately prior to injecting the therapeutic fluid into the patient. That is, it is customary to withdraw the plunger 46 a short distance in the direction of arrow 70 (FIG. 3C) to create a vacuum in the chamber 30 which serves to draw body fluids into the chamber. In the event blood is drawn, this indicates that the needle is undesirably in a blood vessel. This requires that the needle be withdrawn from the patient and reinserted at a different location. The procedure indicated in FIGS. 3A, 3B, and 3C is repeated until no blood is drawn into the chamber 30. Once this has been achieved, the plunger 46 is advanced to an extreme position within the barrel member 22 at which point capsule 64 is pushed into contact with the proximal end of the needle in well 43 and the proximal end 38 of the needle 34 pierces the capsule 64. With continued movement of the plunger 46 in the direction of the arrow 68 (FIG. 3D), the capsule 64 becomes deformed to a collapsed state projecting partially into well 43 whereby substantially all of the therapeutic fluid within the capsule is ejected through the needle 34 into the body of the patient.

In the procedure just described, it will be appreciated that as the plunger 46 is being advanced in the direction of the arrow 68 as depicted in FIGS. 3A and 3B, the O-ring seal 62 is forced against the proximal collar member 54. In this position, even though the seal 62 generally prevents the flow of air from the chamber 30 to the surrounding atmosphere, it is ineffective to seal off flow through the air flow channel 60. Therefore, air within the chamber 30 is caused to by-pass the seal ring 62 and to exit to the atmosphere via the air flow channel 60 as the plunger 46 moves toward the front wall 24. However, as the plunger 46 is withdrawn from the barrel member 22 in the direction of the arrow 70, the seal 62 is in engagement with the distal collar member 52 and wall 28 such that air flow channel 60 is sealed against allowing flow of air from the chamber 30 to the surrounding atmosphere. With continued movement of the plunger 46 in the direction of the arrow 70, the chamber 30 becomes larger but without any increase in the air contained therein with the result that a partial vacuum is created, enabling aspiration to take place.

Referring to FIGS. 4A, 4B, 4C and 4D there is shown an embodiment of the invention by which the hypodermic needle may be retracted into the syringe housing after use to prevent accidental piercing of the skin of a person coming into contact with the syringe. Copending application Ser. No. 11,942, now U.S. Pat. No 5,336,198, is directed to a related form of retractable needle syringe. The substance of that application is incorporated herein by reference.

The illustrated syringe system includes a tubular right cylindrical barrel member 71 having a front wall 72 at its distal end partially defining a chamber 73. A hypodermic needle 74 which is sharpened at both ends is secured in slidable engagement in a Luer needle hub 75 which in turn engages a Luer hub connection 76 at the distal end of the syringe barrel member. A flanged swaged fitting 77 is positioned on needle 74 intermediate of its sharpened ends. Luer hub connection 76 has a longitudinal axial passage 78, as best seen in FIG. 4C.

Elongated plunger 79, which may be of cruciform cross section, is adapted for slidable movement within barrel member 71. The head member of the plunger at its distal end includes a pair of spaced apart disc-like collar members 80 and 81 lying in planes generally perpendicular to the longitudinal axis of the plunger and separated by a central core or spindle 82. The outer diameters of collar members 80 and 81 are less than the inside diameter of the barrel member. Air flow passages 83 are formed in collar 81. A sealing member in the form of a resilient washer 84 of rectangular cross section as shown, or an O-ring, is located in the annular space between collars 80 and 81 and surrounding spindle 82. When the plunger is moved in the distal direction shown by the arrow in FIG. 4B washer 84 is in engagement with collar 81. As the plunger moves forward air within the barrel chamber 73 may pass around the periphery of collar 80, through the annular space between the inside perimeter of washer 84 and spindle 82, and out through air vents 83 to the surrounding atmosphere. When the plunger is moved in the opposite or proximal direction as shown by the arrow in FIG. 4A, sealing washer 84 is in fluid tight sealing engagement with both the inside wall of barrel member 71 and the proximal side of distal collar 80. Thus, as the plunger is withdrawn negative pressure is created within chamber 73. When the plunger is withdrawn after needle 74 has been inserted into the tissue of a living body, if the needle has struck a blood vessel, blood will be aspirated into chamber 73 signaling the user to withdraw the syringe and insert it in a different location.

In this form of safety syringe a needle extractor cup 85 is located within barrel chamber 73. Cup 85 is of circular cross section having an annular side wall with an outside diameter slightly less than the inside diameter of the chamber to permit a loose slide fit and a distal front wall corresponding generally to the corresponding front wall of the chamber. Cup 85 has a distally or forwardly extending tubular needle extractor 85A extending with a loose slide fit into passage 78 of the hub 76 of barrel member 71.

The inside diameter of the forward or distal end of needle extractor 85A corresponds to the diameter of the hub of swaged fitting 77 to engage the same in tight frictional engagement. As disclosed and illustrated in the aforesaid copending application, the distal end of Luer connection 76 is tapered slightly inwardly and has a series of longitudinal slots separating the distal end of the connection into plural segments 87. When the tip of extractor 85A is brought into engagement with needle fitting 77 segments 87 are expanded outwardly, as seen in FIG. 4B, enlarging the distal end of axial passage 78 to permit the flange of fitting 77 to be drawn into and through passage 78, as seen in FIG. 4C. The hub of swaged needle fitting 77 and/or the inside distal end of extractor 85A may be knurled or serrated to insure better engagement between them.

The proximal end of cup 85 is provided with an inturned deformable flanged lip 86. The inside perimeter of lip 86 defines an entry passage into the cup and is slightly less than the outside diameter of distal collar 80. The outside diameter of distal collar 80 in turn is less than the inside diameter of cup 84 to permit the collar 80 to easily fit therein. When the plunger is moved forwardly in the distal direction as shown by the arrow in FIG. 4B, the distal collar 80 expands the proximal end of cup 85 and deforms or deflects the lip 86 to pass into the cup. When the plunger is withdrawn as shown in FIG. 4C, the proximal edge of distal collar 80 engages the inside edge of lip 86 and withdraws the cup and needle along with the plunger. When the front wall 72 of the barrel member tapers inwardly and forwardly as shown, the distal face of distal collar 80 is preferably shaped to conform.

As heretofore described, a predetermined dose of a therapeutic fluid is enveloped within a collapsible capsule 64 of gelatin or comparable biocompatible film forming encapsulating material. Capsule 64 may simply be dropped into the chamber of barrel member 71 into cup 84 prior to insertion of plunger 79. The plunger is pushed forwardly into the barrel member, but not so far as to engage the capsule. Then needle 74 is inserted into the tissue of the body to be injected and, as shown in FIG. 4A, the plunger is withdrawn to create a vacuum within chamber 73. If no blood is aspirated into the syringe the plunger is pushed forwardly to bring capsule 64 into piercing engagement with the inner sharpened end of needle 74 within extractor tube 85.

As the plunger moves forwardly, capsule 64 is collapsed and its contained fluid injected into the body. As shown in FIG. 4B extractor tube 85 engages the hub of needle fitting 77, being shown just before the final thrust of the plunger before the fluid is completely expelled from the capsule and the extractor tube is in firm engagement with the needle. Then, as shown in FIG. 4C, when the plunger is withdrawn cup 85 and extractor tube 85A are drawn into the barrel member along with needle 74 which is safely enclosed to prevent accidental piercing of anyone later handling the syringe.

Yet another embodiment of the invention is illustrated in FIGS. 5A and 5B. This embodiment is intended as an alternative construction to permit aspiration of the syringe system generally in the manner as disclosed above by means of FIGS. 3A, 3B, 3C, and 3D. However, in this instance, a modified head member 88 of a plunger 90 is slideably engaged with a barrel member 94. A seal 96 is in the form of a tapered flexible annular feather flange which is integral with the plunger 90. The entire structure of the plunger 90 including the head member 88 and the seal 96 is preferably of a resilient material. The seal 96 is so sized that its extreme peripheral edge 98 firmly engages the inner wall 100 of the barrel member 94 in fluid tight sealing engagement. It will be appreciated that as the plunger 90 is moved toward the right, viewing FIG. 5A, air in the chamber 102 can be caused to exit by flowing around and between the thin feathered peripheral edge 98 and the inner wall 100. That is, the seal 96 is sufficiently flexible that pressure in the chamber 102 can be effective to tend to flatten the peripheral edge 98 toward the outer surface of the head member 88. However, when the plunger 90 is retracted, the peripheral edge 98 is caused to "dig in" or firmly engage the inner wall 100 with the result that the flow of air between the chamber 102 and the surrounding atmosphere is prevented. This results in the formation of a partial vacuum in the chamber 102 thereby enabling aspiration to take place.

It is apparent that many modifications and variations of this invention as hereinbefore set forth may be made without departing from the spirit and scope thereof. The specific embodiments described are given by way of example only and the invention is limited only by the terms of the appended claims.

We claim:

1. A hypodermic syringe system for injecting a predetermined amount of a therapeutic fluid into tissue of a living body comprising:
   A) an elongated plunger extending between a proximal end and a distal end and having:
      1) a piston-like head member on said distal end and
      2) a thumb plate on said proximal end;
   B) a one-piece unitary elongated barrel member having a longitudinal axis and extending between a distal end and a proximal end and defining a smooth walled cylindrical chamber of uniform diameter for slidably receiving said distal end of said plunger therein, said barrel member including:
      1) a front wall at said distal end thereof,
      2) an outwardly extending rim at said proximal end defining a breech-loading opening through which said distal end of said plunger can extend, and
      3) a hub member integral with said front wall mounting a double ended hypodermic needle including a first sharpened end for piercing engagement with the body tissue and a second sharpened end opposite said first end, the tip of said second end extending through the front wall of the barrel member, said needle being in substantial alignment with the longitudinal axis of said barrel member; and C) a sealed collapsible needle-penetrable capsule containing a predetermined dose of the therapeutic liquid to be injected, said capsule loosely fitting within the chamber of said barrel member between the head member of said plunger and the tip of the second end of said needle, said capsule being insertable through the breech-loading opening of the barrel prior to insertion of the plunger.

2. A syringe system according to claim 1 wherein the head member of said plunger includes sealing means in fluid tight sealing engagement with the wall of the chamber of said barrel member when said plunger is moved in the proximal direction to form a vacuum within the chamber, and having means to permit escape of air from said chamber when said plunger is moved in the distal direction.

3. A syringe system according to claim 2 wherein:
A) said head member includes proximal and distal generally parallel, spaced apart, collar members lying in planes generally perpendicular to the longitudinal axis and having an annular recess which is generally co-axial with the longitudinal axis when said plunger is positioned in the chamber;
B) an annular resilient sealing member in said recess,
 1) the outer periphery of said sealing member being in fluid tight sealing engagement with the wall of the chamber, and
 2) said sealing member being movable from a first position engageable with the distal collar member and a second position in engagement with the proximal collar member; and
C) air passage means in said proximal collar member sealable against passage of air when said annular sealing member is in engagement with said distal member.

4. A syringe system according to claim 3 wherein said sealing member is an O-ring.

5. A syringe system according to claim 3 wherein said sealing member is a washer of rectangular cross-section.

6. A syringe system according to claim 2 wherein said sealing member is a tapered resilient feather flange valve on the head member of said plunger.

7. A syringe system according to claim 1 wherein:
A) said needle is supported in a separable needle hub engageable with the hub member of said barrel member and includes a flanged swaged fitting intermediate of the ends of the needle;
B) the hub of said barrel member includes an axial longitudinal passage;
C) a cup member fitted with a loose slide fit is disposed in the chamber of said barrel member between the front wall thereof and the front face of said plunger, the inside diameter of said cup being greater than the outside diameter of the head member of the plunger, said cup including:
 1) a tubular needle extractor extending in the distal direction in a loose slide fit within the axial passage within the barrel hub, the distal end of said extractor being engageable with the swaged fitting of the needle, and
 2) an axial inwardly extending deflectable lip at the proximal end defining a deformable cup opening of inside diameter less than the outside diameter of the head member of the plunger; and
D) said capsule is disposed within said cup.

8. A syringe system according to claim 1 wherein the distal surface of the head member of said plunger is shaped to conform to the proximal surface of the front wall of said barrel member.

9. A syringe system according to claim 8 wherein said surfaces taper inwardly toward the longitudinal axis of the barrel member and forwardly toward the distal end thereof.

10. A hypodermic syringe system for injecting a therapeutic fluid into tissue of a living body comprising:
A) a one-piece unitary elongated tubular barrel member having a longitudinal axis and extending between a front wall at the distal end and an annular operating outwardly extending flange at the proximal end and including an inner wall defining a smooth walled cylindrical chamber of uniform diameter therein, said operating flange defining a breech-loading opening into the chamber;
B) a hypodermic needle including a first sharpened end for piercing engagement with the body tissue;
C) a hub member integral with said front wall for mounting said needle so as to be substantially aligned with said longitudinal axis;
D) an elongated plunger for slidable reception through the proximal opening into the chamber of said barrel, said plunger extending between a proximal end and a distal end and including a piston-like head member on said distal end and a thumb plate on said proximal end; and
E) said head member including sealing means in fluid tight sealing engagement with the wall of the chamber of said barrel member when said plunger is moved in the proximal direction to form a vacuum within the chamber between the head member and front wall of the barrel member, and having means to permit escape of air from said chamber through or around said head member when said plunger is moved in the distal direction.

11. A syringe system according to claim 10 wherein:
A) said head member includes proximal and distal generally parallel, spaced apart, collar members lying in planes generally perpendicular to the longitudinal axis and having an annular recess which is generally co-axial with the longitudinal axis when said plunger is positioned in the chamber;
B) an annular resilient sealing member in said recess,
 1) the outer periphery of said sealing member being in fluid tight engagement with the wall of the chamber,
 2) said sealing member being moveable from a first position in engagement with the distal collar member and a second position in engagement with the proximal collar member; and
C) air passage means in said proximal collar member sealable against passage of air when said annular sealing member is in engagement with said distal member.

12. A syringe system according to claim 11 wherein said sealing member is an O-ring.

13. A syringe system according to claim 11 wherein said sealing member is a washer of rectangular cross-section.

14. A sealing system according to claim 10 wherein said sealing member is a tapered resilient feather flange valve on the head member of said plunger.

15. A syringe system according to claim 10 wherein:
A) said hypodermic needle includes a first sharpened end for insertion into the living body and a second sharpened end projecting into the chamber; and B) a sealed capsule containing a predetermined dosage of the therapeutic fluid to be injected is disposed in the chamber of said barrel member between said head member and the tip of the second end of said needle.

16. A syringe system according to claim 15 wherein:
A) said needle is supported in a separable needle hub engageable with the hub member of said barrel member and includes a flanged swaged fitting intermediate of the ends of the needle;
B) the hub of said barrel member includes an axial longitudinal passage;
C) a cup member fitted with a loose slide fit is disposed in the chamber of said barrel member between the front wall thereof and the front face of said plunger, the inside diameter of said cup being greater than the outside diameter of the head member of the plunger, said cup including:
 1) a tubular needle extractor extending in the distal direction in a loose slide fit within the axial passage within the barrel hub, the distal end of said extractor being engageable with the swaged fitting of the needle, and
 2) an annular inwardly extending deflectable lip at the proximal end defining a deformable cup opening of inside diameter less than the outside diameter of the head member of the plunger; and
D) said capsule is disposed within said cup.

17. A syringe system according to claim 10 wherein the distal surface of the head member of said plunger is shaped to conform to the proximal surface of the front wall of said barrel member.

18. A syringe system according to claim 17 wherein said surfaces taper inwardly toward the longitudinal axis of the barrel member and forwardly toward the distal end thereof.

* * * * *